(12) United States Patent
Olenik et al.

(10) Patent No.: US 9,783,534 B2
(45) Date of Patent: Oct. 10, 2017

(54) CRYSTALLINE FORM OF 2-{3-[2-(1-{[3,5-BIS (DIFLUOROMETHYL)-1H-PYRAZOL-1-YL] ACETYL}PIPERIDIN-4-YL)-1, 3-THIAZOL-4-YL]-4,5-DIHYDRO-1,2-OXAZOL-5-YL}-3-CHLOROPHENYLMETHANESULPHONATE

(71) Applicant: BAYER CROPSCIENCE AKTIENGESELLSCHAFT, Monheim am Rhein (DE)

(72) Inventors: Britta Olenik, Bottrop (DE); Stefan Hillebrand, Neuss (DE); Pierre Wasnaire, Duesseldorf (DE); Martin Weiss, Bornheim/Schtem (DE); Ulrike Wachendorff-Neumann, Neuwied (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/028,923

(22) PCT Filed: Oct. 13, 2014

(86) PCT No.: PCT/EP2014/071874
§ 371 (c)(1),
(2) Date: Apr. 12, 2016

(87) PCT Pub. No.: WO2015/055574
PCT Pub. Date: Apr. 23, 2015

(65) Prior Publication Data
US 2016/0251344 A1    Sep. 1, 2016

(30) Foreign Application Priority Data

Oct. 17, 2013  (EP) .................................... 13189076
Jul. 2, 2014   (EP) .................................... 14175455

(51) Int. Cl.
*C07D 417/14*   (2006.01)
*A01N 43/80*    (2006.01)

(52) U.S. Cl.
CPC ........... *C07D 417/14* (2013.01); *A01N 43/80* (2013.01); *C07B 2200/13* (2013.01)

(58) Field of Classification Search
None
See application file for complete search history.

(56) References Cited

U.S. PATENT DOCUMENTS

| | | |
|---|---|---|
| 8,759,527 B2 | 6/2014 | Tsuchiya et al. |
| 9,006,266 B2 | 4/2015 | Tsuchiya et al. |
| 9,150,565 B2 | 10/2015 | Tsuchiya et al. |
| 2013/0296272 A1* | 11/2013 | Tsuchiya .............. C07D 417/14 514/326 |
| 2015/0175598 A1 | 6/2015 | Tsuchiya et al. |
| 2015/0313225 A1* | 11/2015 | Lohmann ................ A01N 37/42 504/100 |
| 2015/0327549 A1* | 11/2015 | Wachendorff-Neumann ............................. A01N 43/80 504/116.1 |
| 2015/0351403 A1 | 12/2015 | Tsuchiya et al. |

FOREIGN PATENT DOCUMENTS

| | | | | |
|---|---|---|---|---|
| DE | WO 2012025557 A1 * | 3/2012 | ............. | A01N 43/80 |
| WO | 2012025557 A1 | 3/2012 | | |
| WO | 2013127704 A1 | 9/2013 | | |

OTHER PUBLICATIONS

International Search Report from corresponding PCT/EP2014/071874, mailed Nov. 27, 2014.
Caira et al., "Crystalline Polymorphism of Organic Compounds" Topics in Current Chemistry. (Feb. 26, 1998) vol. 198: 163-208.

* cited by examiner

Primary Examiner — Jeffrey S Lundgren
Assistant Examiner — Michael Schmitt
(74) Attorney, Agent, or Firm — McBee Moore Woodward Vanik IP, LLC (57) ABSTRACT

The present invention relates to a novel crystalline form of 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenylmethansulphonate, to processes for its preparation and to its use in agrochemical preparations.

10 Claims, 1 Drawing Sheet

CRYSTALLINE FORM OF 2-{3-[2-(1-{[3,5-BIS (DIFLUOROMETHYL)-1H-PYRAZOL-1-YL] ACETYL}PIPERIDIN-4-YL)-1, 3-THIAZOL-4-YL]-4,5-DIHYDRO-1,2-OXAZOL-5-YL}-3-CHLOROPHENYLMETHANESULPHONATE

CROSS REFERENCE TO RELATED APPLICATIONS

This application is a §371 National Stage Application of PCT/EP2014/071874, filed 13 Oct. 2014 which claims priority to EP 13189076.6, filed 17 Oct. 2013 and 14175455.6, filed Jul. 2, 2014.

BACKGROUND

Field of the Invention

The present invention relates to a novel crystalline form of 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenylmethanesulphonate, to a process for the preparation of this novel crystalline form, to the advantageous use for the preparation of stable application forms, and to the use thereof for controlling plant-pathogenic harmful fungi in and/or on plants or in and/or on seed of plants.

Description of Related Art

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate The compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate and methods for preparing this compound are known. It is also known that this compound has fungicidal action. Thus, for example WO 2012/025557 describes for the first time the preparation of this compound and its use for controlling plant-pathogenic harmful fungi in and/or on plants or in and/or on seed of plants.

Moreover, it is known that the compound 2-{3-[2-(1-{[3, 5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate can be used in mixtures with other fungicides: WO 2013/127704.

2-{3-[2-(1-{[3,5-Bis(difluoromethyl)-1H-pyrazol-1-yl] acetyl}piperidin-4-yl)-1,3-thiazol-4-yl]-4,5-dihydro-1,2-oxazol-5-yl}-3-chlorophenylmethanesulphonate from WO 2012/025557 is in the form of an amorphous solid. It can be used either in formulations, such as emulsion concentrates (EC), in which the solid is dissolved, or else in formulations in which the active ingredient is furthermore present in solid form (solid formulation). These are, for example, granules, encapsulated granules, tablets, water-dispersible granules, water-dispersible tablets, water-dispersible powders or water-dispersible powders for the treatment of seed, dust formulations, formulations in which the active ingredient is present in dispersed form, such as, for example: suspension concentrates (SC), oil-based suspension concentrates, suspoemulsions or suspension concentrates for the treatment of seed.

In principle, solid formulation are of great economic relevance since they have a very good storage stability. However, this is only the case if the active ingredient is present in amorphous form and thus not in the most thermodynamically stable modification.

Since the ecological and economic requirements placed on modern crop protection compositions are continually increasing, for example as regards the action spectrum, activity and application rate, it would be desirable to have present, besides the amorphous form, a further modification of the active ingredient 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate which, in a solid formulation, has advantages, at least in part areas, compared with the known ones.

SUMMARY

Surprisingly, a new crystalline form of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate has now been found which avoids the aforementioned disadvantages of the storage stability in a solid formulation and has improved fungicidal activity compared with the amorphous form in a solid formulation.

The invention therefore relates to the novel crystalline form of the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate which is characterized in that it has the X-ray powder diffractogram (see FIG. 1) of this compound at 25 C and use of Cu-Kα radiation (1.54 Å) at least 3, in particular at least 4 or 6 and preferably all of the following 2Θ (2 theta) values (Table 1):

TABLE 1

Figure 1:
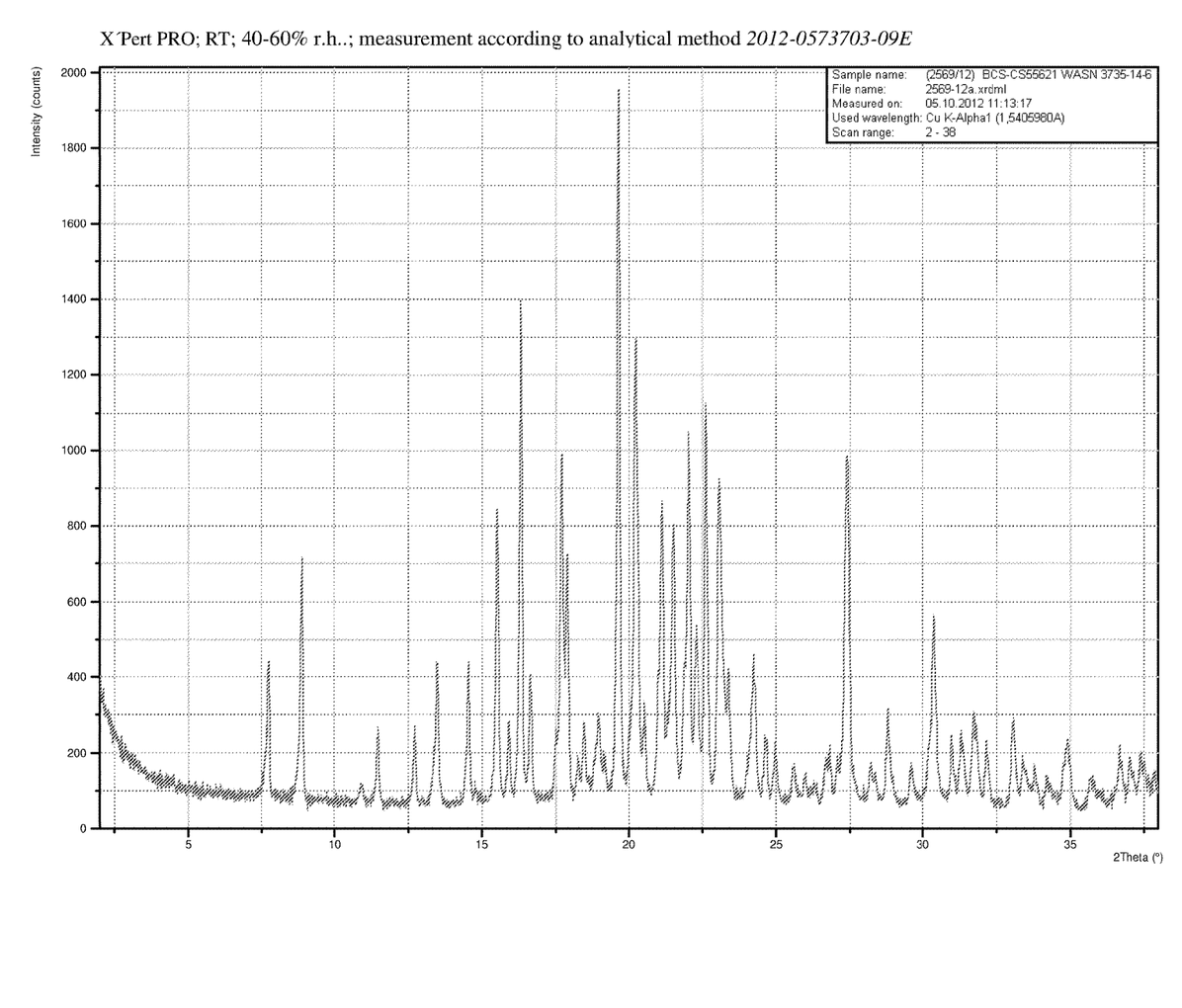
FIG. 1: X-ray powder diffractogram of the novel crystalline form of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate.

| |
|---|
| 2Θ = 7.75° ± 0.2 |
| 2Θ = 8.89 ± 0.2 |
| 2Θ = 10.91 ± 0.2 |
| 2Θ = 11.45 ± 0.2 |
| 2Θ = 12.72 ± 0.2 |
| 2Θ = 13.46 ± 0.2 |
| 2Θ = 14.54 ± 0.2 |
| 2Θ = 14.75 ± 0.2 |
| 2Θ = 15.53 ± 0.2 |
| 2Θ = 15.90 ± 0.2 |
| 2Θ = 16.33 ± 0.2 |
| 2Θ = 16.65 ± 0.2 |
| 2Θ = 17.49 ± 0.2 |
| 2Θ = 17.71 ± 0.2 |
| 2Θ = 17.89 ± 0.2 |
| 2Θ = 18.27 ± 0.2 |
| 2Θ = 18.47 ± 0.2 |
| 2Θ = 18.86 ± 0.2 |
| 2Θ = 18.99 ± 0.2 |
| 2Θ = 19.18 ± 0.2 |
| 2Θ = 19.63 ± 0.2 |
| 2Θ = 20.03 ± 0.2 |
| 2Θ = 20.22 ± 0.2 |
| 2Θ = 20.53 ± 0.2 |
| 2Θ = 21.11 ± 0.2 |
| 2Θ = 21.32 ± 0.2 |
| 2Θ = 21.50 ± 0.2 |
| 2Θ = 21.84 ± 0.2 |
| 2Θ = 22.01 ± 0.2 |
| 2Θ = 22.28 ± 0.2 |
| 2Θ = 22.61 ± 0.2 |
| 2Θ = 23.05 ± 0.2 |
| 2Θ = 23.39 ± 0.2 |
| 2Θ = 24.02 ± 0.2 |
| 2Θ = 24.22 ± 0.2 |
| 2Θ = 24.62 ± 0.2 |
| 2Θ = 24.97 ± 0.2 |
| 2Θ = 25.59 ± 0.2 |
| 2Θ = 25.99 ± 0.2 |
| 2Θ = 26.31 ± 0.2 |
| 2Θ = 26.67 ± 0.2 |

TABLE 1-continued

2Θ = 26.85 ± 0.2
2Θ = 27.07 ± 0.2
2Θ = 27.43 ± 0.2
2Θ = 28.21 ± 0.2
2Θ = 28.34 ± 0.2
2Θ = 28.78 ± 0.2
2Θ = 29.59 ± 0.2
2Θ = 30.19 ± 0.2
2Θ = 30.37 ± 0.2
2Θ = 30.96 ± 0.2
2Θ = 31.29 ± 0.2
2Θ = 31.70 ± 0.2
2Θ = 31.81 ± 0.2
2Θ = 32.16 ± 0.2
2Θ = 33.02 ± 0.2
2Θ = 33.39 ± 0.2
2Θ = 33.64 ± 0.2
2Θ = 33.79 ± 0.2
2Θ = 33.80 ± 0.2
2Θ = 34.20 ± 0.2
2Θ = 34.77 ± 0.2
2Θ = 34.89 ± 0.2
2Θ = 35.66 ± 0.2
2Θ = 35.95 ± 0.2
2Θ = 36.67 ± 0.2
2Θ = 37.03 ± 0.2
2Θ = 37.38 ± 0.2
2Θ = 37.51 ± 0.2
2Θ = 37.87 ± 0.2

DETAILED DESCRIPTION OF A PREFERRED EMBODIMENT

The novel crystalline form has, in addition to the 2 theta values, the lattice plane spacings "d" listed in Table 2.

TABLE 2

2 theta values and lattice plane spacings "d" of the novel crystalline form of the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, determined by X-ray powder diffractometry.

| 2Θ | d value [Å] |
|---|---|
| 7.75° ± 0.2 | 11.41 ± 0.1 |
| 8.89 ± 0.2 | 9.95 ± 0.1 |
| 10.91 ± 0.2 | 8.11 ± 0.1 |
| 11.45 ± 0.2 | 7.73 ± 0.1 |
| 12.72 ± 0.2 | 6.96 ± 0.1 |
| 13.46 ± 0.2 | 6.58 ± 0.1 |
| 14.54 ± 0.2 | 6.09 ± 0.1 |
| 14.75 ± 0.2 | 6.00 ± 0.1 |
| 15.53 ± 0.2 | 5.71 ± 0.1 |
| 15.90 ± 0.2 | 5.57 ± 0.1 |
| 16.33 ± 0.2 | 5.43 ± 0.1 |
| 16.65 ± 0.2 | 5.33 ± 0.1 |
| 17.49 ± 0.2 | 5.07 ± 0.1 |
| 17.71 ± 0.2 | 5.01 ± 0.1 |
| 17.89 ± 0.2 | 4.96 ± 0.1 |
| 18.27 ± 0.2 | 4.86 ± 0.1 |
| 18.47 ± 0.2 | 4.80 ± 0.1 |
| 18.86 ± 0.2 | 4.70 ± 0.1 |
| 18.99 ± 0.2 | 4.67 ± 0.1 |
| 19.18 ± 0.2 | 4.63 ± 0.1 |
| 19.62 ± 0.2 | 4.52 ± 0.1 |
| 20.03 ± 0.2 | 4.43 ± 0.1 |
| 20.22 ± 0.2 | 4.39 ± 0.1 |
| 20.53 ± 0.2 | 4.33 ± 0.1 |
| 21.11 ± 0.2 | 4.21 ± 0.1 |
| 21.32 ± 0.2 | 4.16 ± 0.1 |
| 21.50 ± 0.2 | 4.13 ± 0.1 |
| 21.84 ± 0.2 | 4.07 ± 0.1 |
| 22.01 ± 0.2 | 4.04 ± 0.1 |
| 22.28 ± 0.2 | 3.99 ± 0.1 |
| 22.61 ± 0.2 | 3.93 ± 0.1 |
| 23.05 ± 0.2 | 3.86 ± 0.1 |
| 23.39 ± 0.2 | 3.80 ± 0.1 |
| 24.02 ± 0.2 | 3.70 ± 0.1 |
| 24.22 ± 0.2 | 3.67 ± 0.1 |
| 24.62 ± 0.2 | 3.62 ± 0.1 |
| 24.97 ± 0.2 | 3.57 ± 0.1 |
| 25.59 ± 0.2 | 3.48 ± 0.1 |
| 25.99 ± 0.2 | 3.43 ± 0.1 |
| 26.31 ± 0.2 | 3.39 ± 0.1 |
| 26.67 ± 0.2 | 3.34 ± 0.1 |
| 26.85 ± 0.2 | 3.32 ± 0.1 |
| 27.07 ± 0.2 | 3.29 ± 0.1 |
| 27.43 ± 0.2 | 3.25 ± 0.1 |
| 28.21 ± 0.2 | 3.16 ± 0.1 |
| 28.34 ± 0.2 | 3.15 ± 0.1 |
| 28.78 ± 0.2 | 3.10 ± 0.1 |
| 29.59 ± 0.2 | 3.019 ± 0.1 |
| 30.19 ± 0.2 | 2.96 ± 0.1 |
| 30.37 ± 0.2 | 2.94 ± 0.1 |
| 30.96 ± 0.2 | 2.89 ± 0.1 |
| 31.29 ± 0.2 | 2.86 ± 0.1 |
| 31.70 ± 0.2 | 2.82 ± 0.1 |
| 31.81 ± 0.2 | 2.81 ± 0.1 |
| 32.16 ± 0.2 | 2.78 ± 0.1 |
| 33.02 ± 0.2 | 2.71 ± 0.1 |
| 33.39 ± 0.2 | 2.68 ± 0.1 |
| 33.64 ± 0.2 | 2.66 ± 0.1 |
| 33.79 ± 0.2 | 2.66 ± 0.1 |
| 33.80 ± 0.2 | 2.65 ± 0.1 |
| 34.20 ± 0.2 | 2.62 ± 0.1 |
| 34.77 ± 0.2 | 2.58 ± 0.1 |
| 34.89 ± 0.2 | 2.57 ± 0.1 |
| 35.66 ± 0.2 | 2.52 ± 0.1 |
| 35.95 ± 0.2 | 2.50 ± 0.1 |
| 36.67 ± 0.2 | 2.45 ± 0.1 |
| 37.03 ± 0.2 | 2.43 ± 0.1 |
| 37.38 ± 0.2 | 2.40 ± 0.1 |
| 37.51 ± 0.2 | 2.40 ± 0.1 |
| 37.87 ± 0.2 | 2.37 ± 0.1 |

Surprisingly, it has been found that 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form is sufficiently thermodynamically stable for economically relevant use and is not converted into another form even on prolonged storage.

This allows the preparation of suspension concentrates, oil-based suspension concentrates and, for example, water-dispersible granules and similar formulations for the treatment of seed.

The compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, in the novel crystalline form, is outstandingly suitable, on account of its stability, for the preparation of compositions for controlling plant-pathogenic harmful fungi in and/or on plants or in and/or on seed of plants. The invention therefore also provides compositions for controlling plant-pathogenic harmful fungi in and/or on plants or in and/or on seed of plants, which comprise the novel crystalline form alone or in a mixture with auxiliaries and carriers, and in a mixture with other active ingredients.

The invention also includes compositions which comprise the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form. Preference is given to compositions comprising less than 20% by weight of the novel solid form, particularly preferably less than 15% by weight, very particularly preferably less than 10% by weight, especially preferably less than 5% by weight and most preferably less than 4, 3, 2 or 1% by weight of the novel crystalline form. The term "composition" also comprises formulations and use forms.

Furthermore, the invention also relates to processes for the preparation of compositions for controlling plant-pathogenic harmful fungi in and/or on plants or in and/or on seed of plants, which use the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form. By using the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form, the safety for preparations which comprise the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate is increased and thus the risk of incorrect dosages is reduced.

The compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form can be converted in a known manner into the customary formulations, such as suspension concentrates, oil-based suspension concentrates, colloidal concentrates, dispersible concentrates, emulsifiable concentrates (emulsion concentrates), emulsion dressings, suspension dressings, granules, microgranules, suspoemulsions, water-soluble granules, water-soluble concentrates and water-dispersible granules, and also corresponding ready-to-use formulations, using suitable auxiliaries and carriers or solvents. In this connection, the active compound should be present in a concentration of approximately 0.0001 to 90% by weight of the total mixture, i.e. in amounts which are sufficient in order to achieve the dosage level required. The formulations are prepared, for example, by extending the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form with water, solvents and/or carriers, using, if appropriate, emulsifiers and/or dispersants, and/or other auxiliaries, such as, for example, penetrants.

In the production of suspension concentrates, including those which are used for seed treatment, further assistants are generally added as well as the active ingredient and an extender (water, solvent or oil). A wetting agent is used to moisten the active ingredient in the continuous phase, dispersants are used to stabilize the suspension in the liquid phase, emulsifiers are used to emulsify the non-aqueous phase of solvent- or oil-comprising suspension concentrates. If required, antifreeze agents, biocides, thickeners, colorants, spreading agents and/or penetrants are incorporated.

The novel solid compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate is obtained by the method described below. The compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate is prepared as described for example in WO2012/025557. The 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate thus obtained is in the amorphous state.

To prepare the compound according to the invention, amorphous 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate is suspended in a solvent or a solvent mixture at temperatures of at least 50° C., preferably at least 80° C., and slowly cooled until the desired crystals precipitate out. The amount of the solvent used is chosen such that the mixture remains readily stirrable during the crystallization.

The slow cooling takes place linearly or step-wise. Preferably, the cooling takes place linearly, where the crystallization solution is stirred at a certain temperature, preferably at about 20° C., for a number of hours, preferably for 5 to 25 hours, particularly preferably for 15 to 20 hours, very particularly preferably for 16 to 17 hours, before they are cooled further until the desired crystals precipitate out.

Seed crystals are optionally added to the suspension in order to promote crystallization. The addition of the seed crystals can in principle take place during stirring.

Suitable solvents are halogenated hydrocarbons (for example chlorobenzene, bromobenzene, dichlorobenzene, chlorotoluene, trichlorobenzene), ethers (for example ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-THF and polyethers of ethylene oxide and/or propylene oxide), nitrohydrocathons (for example nitromethane, nitroethane, nitropropane, nitrobenzene, chloronitrobenzene, o-nitrotoluene), aliphatic, cycloaliphatic or aromatic hydrocarbons (for example pentane, n-hexane, n-heptane, n-octane, nonan, for example white spirits with components having boiling points in the range, for example, of from 40° C. to 250° C., cymene, petroleum fractions within a boiling range of from 70° C. to 190° C., cyclohexane, methylcyclohexane, petroleum ether, ligroin, octane, benzene, toluene, xylene), esters (for example malonates, acetic acid n-butyl ester (n-butyl acetate), methyl acetate, ethyl acetate, isobutyl acetate, dimethyl carbonate, diethyl carbonate, dibutyl carbonate, ethylene carbonate); and aliphatic alcohols (for example methanol, ethanol, n-propanol and isopropanol and n-butanol, tert-amyl alcohol). Preferred solvents are ethers, aromatic hydrocarbons such as benzene, toluene, xylene, chlorobenzene, esters and aliphatic alcohols and mixtures thereof. Particularly preferred solvents or solvent mixtures are isopropanol, toluene, methyl-THF, diethyl carbonate, chlorobenzene, n-butyl acetate and isobutyl acetate, n-butanol, ethanol, ethyl malonate, methyl t-butyl ether, and also mixtures of toluene and butanol, toluene and n-butyl acetate, ethyl malonate and methyl t-butyl ether, and butyl acetate and methyl t-butyl ether. Solvent mixtures with more than 2 components are also possible.

Besides the aforementioned formulations, the compound 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form can be converted into other formulations. Such formulations are, for example, solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances. Preference according to the invention is given to solid formulations.

The formulations are produced in a known manner, for example by mixing the active ingredients with extenders, that is, liquid solvents and/or solid carriers, optionally with the use of surfactants, that is to say wetting agents, emulsifiers, dispersants and/or antifoams. The formulations are prepared either in suitable facilities or else before or during application.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics, such as xylene, toluene, or alkylnaphthalenes, aliphatic hydrocarbons or paraffins, for example mineral oil fractions, mineral and vegetable oils, alcohols and also their ethers and esters, ketones, such as methyl ethyl ketone, methyl isobutyl ketone or cyclohexanone, strongly polar solvents, such as N-methylpyrrolidone, dimethyl sulphoxide, and also water.

According to the invention, a carrier is a natural or synthetic, organic or inorganic substance which may be solid or liquid and with which the active ingredients are mixed or bonded for better applicability, in particular for application to plants or plant parts or seed. The solid or liquid carrier is generally inert and should be usable in agriculture.

Suitable solid or liquid carriers are:

e.g. ammonium salts and ground natural minerals, such as kaolins, clay earths, talc, chalk, quartz, attapulgite, montmorillonite or diatomaceous earth and synthetic stone flours, such as finely divided silica, alumina and silicates, suitable solid carriers for granules are: e.g. crushed and fractionated natural rocks such as calcite, marble, sand, pumice, sepiolite, dolomite, and synthetic granules from inorganic and organic flours, and granules of organic material such as paper, sawdust, coconut shells, corn cobs and tobacco stalks; suitable emulsifiers and/or foam generators are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolyzates; suitable dispersants are nonionic and/or ionic substances, for example from the classes of the fatty alcohol-POE and/or POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. It is also possible to use lignin and its sulphonic acid derivatives, unmodified and modified celluloses, aromatic and/or aliphatic sulphonic acids and also their adducts with formaldehyde.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The active ingredient content of the use forms prepared from the formulations can vary within wide limits. The active ingredient concentration of the use forms is in the range of from 0.00000001 to 97% by weight of active ingredient, preferably in the range of from 0.0000001 to 97% by weight, particularly preferably in the range of from 0.000001 to 83% by weight or 0.000001 to 5% by weight, and very particularly preferably in the range of from 0.0001 to 1% by weight.

The compound according to the invention 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, in the novel crystalline form, is suitable, coupled with good plant compatibility, favourable warm-blooded animal toxicity and good environmental tolerability, for protecting plants and plant organs, for increasing harvest yields, improving the quality of the harvested product and for controlling plant-pathogenic harmful fungi in and/or on plants or in and/or on seed of plants. Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* or *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plas-* mopara viticola; Pseudoperonospora species, for example Pseudoperonospora humuli or Pseudoperonospora cubensis; Pythium species, for example Pythium ultimum;

leaf blotch diseases and leaf wilt diseases caused, for example, by Alternaria species, for example Alternaria solani; Cercospora species, for example Cercospora beticola; Cladiosporium species, for example Cladiosporium cucumerinum; Cochliobolus species, for example Cochliobolus sativus (conidial form: Drechslera, syn: Helminthosporium) or Cochliobolus miyabeanus; Colletotrichum species, for example Colletotrichum lindemuthanium; Cycloconium species, for example Cycloconium oleaginum; Diaporthe species, for example Diaporthe citri; Elsinoe species, for example Elsinoe fawcettii; Gloeosporium species, for example Gloeosporium laeticolor; Glomerella species, for example Glomerella cingulata; Guignardia species, for example Guignardia bidwelli; Leptosphaeria species, for example Leptosphaeria maculans; Magnaporthe species, for example Magnaporthe grisea; Microdochium species, for example Microdochium nivale; Mycosphaerella species, for example Mycosphaerella graminicola, Mycosphaerella arachidicola or Mycosphaerella fijiensis; Phaeosphaeria species, for example Phaeosphaeria nodomm; Pyrenophora species, for example Pyrenophora teres or Pyrenophora tritici repentis; Ramularia species, for example Ramularia collo-cygni or Ramularia areola; Rhynchosporium species, for example Rhynchosporium secalis; Septoria species, for example Septoria apii or Septoria lycopersici; Stagonospora species, for example Stagonospora nodorum; Typhula species, for example Typhula incarnata; Venturia species, for example Venturia inaequalis;

root and stem diseases caused, for example, by Corticium species, for example Corticium gramineamm; Fusarium species, for example Fusarium oxysporum; Gaeumannomyces species, for example Gaeumannomyces graminis; Plasmodiophora species, for example Plasmodiophora brassicae; Rhizoctonia species, for example Rhizoctonia solani; Sarocladium species, for example Sarocladium olyzae; Sclerotium species, for example Sclerotium olyzae; Tapesia species, for example Tapesia acuformis; Thielaviopsis species, for example Thielaviopsis basicola;

ear and panicle diseases (including corn cobs) caused, for example, by Alternaria species, for example Alternaria spp.; Aspergillus species, for example Aspergillus flavus; Cladosporium species, for example Cladosporium cladosporioides; Claviceps species, for example Claviceps purpurea; Fusarium species, for example Fusarium culmorum; Gibberella species, for example Gibberella zeae; Monographella species, for example Monographella nivalis; Septoria species, for example Septoria nodorum;

diseases caused by smut fungi, for example Sphacelotheca species, for example Sphacelotheca reiliana; Tilletia species, for example Tilletia caries or Tilletia controversa; Urocystis species, for example Urocystis occulta; Ustilago species, for example Ustilago nuda;

fruit rot caused, for example, by Aspergillus species, for example Aspergillus flavus; Botrytis species, for example Botrytis cinerea; Penicillium species, for example Penicillium expansum or Penicillium purpurogenum; Rhizopus species, for example Rhizopus stolonifer; Sclerotinia species, for example Sclerotinia sclerotiorum; Verticilium species, for example Verticilium alboatrum;

seed- and soil-borne rot and wilt diseases, and also diseases of seedlings, caused, for example, by Alternaria species, for example Alternaria brassicicola; Aphanomyces species, for example Aphanomyces euteiches; Ascochyta species, for example Ascochyta lentis; Aspergillus species, for example Aspergillus flavus; Cladosporium species, for example Cladosporium herbarum; Cochliobolus species, for example Cochliobolus sativus (conidial form: Drechslera, Bipolaris Syn: Helminthosporium); Colletotrichum species, for example Colletotrichum coccodes; Fusarium species, for example Fusarium culmomm; Gibberella species, for example Gibberella zeae; Macrophomina species, for example Macrophomina phaseolina; Microdochium species, for example Microdochium nivale; Monographella species, for example Monographella nivalis; Penicillium species, for example Penicillium expansum; Phoma species, for example Phoma lingam; Phomopsis species, for example Phomopsis sojae; Phytophthora species, for example Phytophthora cactorum; Pyrenophora species, for example Pyrenophora graminea; Pyricularia species, for example Pyricularia olyzae; Pythium species, for example Pythium ultimum; Rhizoctonia species, for example Rhizoctonia solani; Rhizopus species, for example Rhizopus olyzae; Sclerotium species, for example Sclerotium rolfsii; Septoria species, for example Septoria nodorum; Typhula species, for example Typhula incarnata; Verticillium species, for example Verticillium dahliae;

cancers, galls and witches' broom caused, for example, by Nectria species, for example Nectria galligena;

wilt diseases caused, for example, by Monilinia species, for example Monilinia laxa;

deformations of leaves, flowers and fruits caused, for example, by Exobasidium species, for example Exobasidium vexans; Taphrina species, for example Taphrina deformans;

degenerative diseases in woody plants, caused, for example, by Esca species, for example Phaeomoniella chlamydospora, Phaeoacremonium aleophilum or Fomitiporia mediterranea; Ganoderma species, for example Ganoderma boninense;

diseases of flowers and seeds caused, for example, by Botrytis species, for example Botrytis cinerea;

diseases of plant tubers caused, for example, by Rhizoctonia species, for example Rhizoctonia solani; Helminthosporium species, for example Helminthosporium solani;

The active ingredient according to the invention also has a very good fortifying action in plants. It is therefore suitable for mobilizing the plant's own defences against attack by undesirable microorganisms.

Plant-fortifying (resistance-inducing) substances are understood to mean, in the present context, those substances which are capable of stimulating the defence system of plants in such a way that the treated plants, when subsequently inoculated with unwanted microorganisms, develop a high degree of resistance to these microorganisms.

In the present case, unwanted microorganisms are understood to mean phytopathogenic fungi and bacteria. The substances according to the invention can thus be used to protect plants for a certain period after the treatment against attack by the pathogens mentioned. The period for which protection is provided generally extends over 1 to 10 days, preferably 1 to 7 days, after the treatment of the plants with the active ingredients.

The fact that the active ingredients are well tolerated by plants at the concentrations required for controlling plant diseases allows the treatment of above-ground parts of plants, of propagation stock and seeds, and of the soil.

The active ingredient according to the invention can be used particularly successfully to control diseases in viticulture and potato, fruit and vegetable growing, for example against powdery mildew fungi, Oomycetes, for example *Phytophthora, Plasmopara, Pseudoperonospora* and *Pythium* species.

The active ingredient according to the invention are also suitable for increasing the harvest yield. In addition, it has low toxicity and is well tolerated by plants.

If appropriate, the compound according to the invention can, at certain concentrations or application rates, also be used as herbicide, safener, growth regulator or agent to improve plant properties, or as microbicide, for example as fungicides, antimycotics, bactericides, viricides (including agents against viroids) or as agents against MLO (*Mycoplasma*-like organisms) and RLO (*Rickettsia*-like organisms). If appropriate, they can also be used as insecticides. If appropriate, they can also be used as intermediates or precursors for the synthesis of other active ingredients.

The treatment according to the invention of the plants and plant parts with the active ingredients or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active ingredients by the ultra-low volume method or to inject the active ingredient preparation or the active ingredient itself into the soil.

Moreover, in the protection of materials, the active ingredient or composition according to the invention can be employed for protecting industrial materials against attack and destruction by unwanted microorganisms, such as, for example, fungi.

Industrial materials in the present context are understood to mean inanimate materials which have been prepared for use in industry. For example, industrial materials which are to be protected by active ingredients according to the invention from microbial alteration or destruction may be adhesives, sizes, paper and board, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the scope of the present invention preferably include adhesives, sizes, papers and cardboard, leather, wood, paints, cooling lubricants and heat transfer fluids, more preferably wood. The active ingredients or compositions according to the invention may prevent adverse effects, such as rotting, decay, discoloration, decoloration or formation of mould.

The method according to the invention for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The active ingredients according to the invention may prevent adverse effects, such as rotting, decay, discoloration, decoloration or formation of mould.

Microorganisms capable of degrading or altering the industrial materials include, for example, bacteria, fungi, yeasts, algae and slime organisms. The active ingredients according to the invention preferably act against fungi, especially moulds, wood-discoloring and wood-destroying fungi (Basidiomycetes), and against slime organisms and algae. Examples include microorganisms of the following genera: *Alternaria*, such as *Alternaria fermis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polypoms*, such as *Polypoms versicolor; Aureobasidium*, such as *Aureobasidium pullulans; Sclerophoma*, such as *Sclerophoma pityophila; Trichoderma*, such as *Trichoderma viride; Escherichia*, such as *Escherichia coli; Pseudomonas*, such as *Pseudomonas aeruginosa; Staphylococcus*, such as *Staphylococcus aureus*.

The fungicidal compositions according to the invention can be used for curative or protective control of phytopathogenic fungi. The invention therefore also relates to curative and protective methods for controlling phytopathogenic fungi through the use of the active ingredients or compositions according to the invention, which are applied to the seed, the plant or plant parts, the fruit or the soil in which the plants grow.

The compositions according to the invention for controlling phytopathogenic fungi in crop protection comprise an effective but non-phytotoxic amount of the inventive active ingredients. An "effective but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the compositions according to the invention.

All plants and plant parts can be treated in accordance with the invention. Plants are understood here to mean all plants and plant populations, such as desired and undesired wild plants or crop plants (including naturally occurring crop plants) Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts shall be understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested material and vegetative and generative propagation material, for example seedlings, tubers, rhizomes, cuttings and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., Oleaceae sp., Actinidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leeks, onions), Papilionaceae sp. (for example peas); major crop plants such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussel sprout, pak choi, kohlrabi, radishes and rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, Swiss chard, beetroot); useful plants and ornamental plants in gardens and forests; and in each case genetically modified types of these plants.

It has been found that mixtures comprising
(A) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in the novel crystalline form and
(B) at least one fungicide selected from the list (see below), not only exhibit a spectrum expanded additively as expected, but moreover also have a synergistic action. Surprisingly, this synergistic effect is more marked than in the case of the mixture of amorphous 2-{3-[2-(1-{[3,5-bis(difluoro methyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in combination with fungicides (WO2013/127704).

Suitable mixing components (B) are in particular the following fungicides:

(1) Inhibitors of ergosterol biosynthesis such as, for example, (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicath, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoro methyl)-2-methyl-4-[3-(trimethylsilyl)propoxy]phenyl}-N-ethyl-N-methylimidofonmamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors) such as, for example, (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS, 4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methano naphthalen-5-yl]-3-(difluoro methyl)-1-methy 1-1H-pyrazole-4-carb oxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3 S)-1,1,3-trimethyl-2,3-dihydro-1H-inden-4-yl]-1H-pyrazole-4-carboxamide, (2.37) 3-(difluoromethyl)-1-methyl-N-[(3 S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3 S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) acting on complex III of the respiratory chain such as, for example, (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanemide, (3.24) (2E)-2-(methoxyimino)-N-methyl-2-(2-{[({(1E)-1-[3-(trifluoromethyl)phenyl]ethylidene}amino)oxy]

methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division such as, for example, (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers such as, for example, (6.1) acibenzolar-S-methyl, (6.2) isotianil, (6.3) probenazole, (6.4) tiadinil and (6.5) laminarin.

(7) Inhibitors of amino acid and protein biosynthesis such as, for example, (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Inhibitors of cell wall synthesis such as, for example, (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Inhibitors of lipid and membrane synthesis such as, for example, (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluo roethyl {3-methyl-1-[(4-methylbenzoyl)amino]butan-2-yl}carbamate.

(12) Inhibitors of nucleic acid synthesis such as, for example, (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors such as, for example, (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers such as, for example, (14.1) binapacryl, (14.2) dinocap, (14.3) ferimzone, (14.4) fluazinam and (14.5) meptyldinocap.

(15) Further compounds such as, for example, (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulphamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulpHamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulphocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5 S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5 S)-5-phenyl-4,5-dihydro-1,2-oxazol-3-yl]-1,3-thiazol-2-yl}piperidin-1-yl)ethanone, (15.64) 2-[5-methyl- 3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(chlorophenyl)-5-(2,6-difluorophenyl)-3,6-dimethylpyridazine, (15.72) 5-amino-1,3,4-thiadiazole-2-thiol, (15.73) 5-chloro-N-phenyl-N-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N'-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl) (phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3 S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3 S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2, 4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5 S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5 S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl) quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl) ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-calboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-calboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3 S)-7-fluoro-1,1,3-trimethyl-2,3-dihydro-1H-inden-4-yl]-1-methyl-1H-pyrazole-4-carboxamide, (15.180) N-(2,5-dimethyl-4-phenoxyphenyl)-N-ethyl-N-methylimidoformamide, (15.181) {4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine.

All mixing partners mentioned in classes (1) to (15) can, if they are capable on the basis of their functional groups, optionally form salts with suitable bases or acids.

All plants and plant parts can be treated in accordance with the invention. Plants are understood here to mean all plants and plant populations, such as desired and undesired wild plants or crop plants (including naturally occurring crop plants) Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants shall be understood to mean all above-ground and below-ground parts and organs of plants, such as shoot, leaf, flower and root, examples including leaves, needles, stems, trunks, flowers, fruit bodies, fruits and seed, and also roots, tubers and rhizomes. The plant parts also include harvested material and vegetative and generative propagation material, for example cuttings, tubers, rhizomes, slips and seed.

Treatment according to the invention of the plants and plant parts with the novel crystalline active ingredient or the active ingredient combinations comprising the novel crystalline active ingredient is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucwbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, lye, rice, barley, oats, millet and triticale), *Asteraceae* sp. (for example sunflower), *Brassicaceae* sp. (for example white cabbage, red cabbage, broccoli, cauliflower, Brussel sprouts, pak choi, kohlrabi, small radishes and oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

Treatment according to the invention of the plants and plant parts with the novel crystalline active ingredient or the active ingredient combinations according to the invention is carried out directly or by allowing the compounds to act on the surroundings, habitat or storage space by the customary treatment methods, for example by immersion, spraying, evaporation, fogging, scattering, painting on and, in the case of propagation material, in particular in the case of seeds, also by applying one or more coats.

Most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The present invention therefore in particular also relates to a method for the protection of seed and germinating plants, from attack by pests, by treating the seed with a composition according to the invention. The invention likewise relates to the use of the compositions according to the invention for the treatment of seed for protecting the seed and the resulting plant from pests. The invention further relates to seed which has been treated with a composition according to the invention for protection from pests. Seed is understood as meaning conventional seed or transgenic seed.

In the case of transgenic seed, the plants originating from this seed are capable of expressing a protein directed against pests. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows efficacy against the European corn borer and/or the corn root worm. It is particularly preferably a heterologous gene derived from *Bacillus thuringiensis*.

By treating such seed with the compositions according to the invention, certain pests can be controlled merely by the expression of the, for example, insecticidal protein, and additionally damage to the seed may be averted by the compositions according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The compositions according to the invention are likewise suitable for treating the seed of fruit plants and vegetables as already mentioned above. The treatment of the seed of maize, soya beans, cotton, wheat and canola or oilseed rape is of particular importance.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, it generally has to be ensured that the amount of the composition according to the invention applied to the seed and/or the amount of further additives is selected such that the germination of the seed is not impaired, or that the resulting plant is not damaged. This must be ensured particularly in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The novel crystalline form of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethansulphonate can be converted to the customary seed dressing formulations, such as solutions, emulsions, suspensions, powders, foams, slurries or other coating materials for seed, and also ULV formulations. These formulations are produced in a known manner, by mixing the active ingredients with customary additives, for example customary extenders and solvents or diluents, dyes, wetting agents, dispersants, emulsifiers, antifoams, preservatives, secondary thickeners, adhesives, gibberellins, and also water.

Colorants which may be present in the seed dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Suitable wetting agents which may be present in the seed dressing formulations which can be used in accordance with the invention are all substances which promote wetting and which are conventionally used for the formulation of agrochemical active ingredients. Preference is given to using alkylnaphthalenesulphonates, such as diisopropyl or diisobutylnaphthalenesulphonates.

Suitable dispersants and/or emulsifiers which may be present in the seed dressing formulations which can be used in accordance with the invention are all nonionic, anionic and cationic dispersants conventionally used for the formulation of agrochemical active ingredients. Nonionic or anionic dispersants or mixtures of nonionic or anionic dispersants are usable with preference. Suitable nonionic dispersants include especially ethylene oxide/propylene oxide block polymers, alkylphenol polyglycol ethers and tristiyiylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical compounds. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schadlingsbekämpfungsmittel", vol. 2, Springer Verlag, 1970, pp. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying operation.

Description of FIG. 1

Preparation of the Novel Solid Form 3 g of amorphous 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form A) (prepared as described in WO2012025557) are admixed with 40 ml of isopropanol and heated to 82° C. Subsequently, the suspension is stirred at this temperature for 10 minutes. The suspension is then left to cool to 20° C. and stirred for a further 16 hours at this temperature. The precipitated crystals are filtered off with suction and dried at room temperature and atmospheric pressure. This gives 2.7 g of crystalline 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form B) with a melting point in the range 153-154° C.

The $^1$H-NMR ($D_6$-DMSO, 298K, 400 MHz) corresponds to that of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in amorphous state as stated in WO 2012/025557.

EXAMPLES

The superiority of the crystalline form over the amorphous form in controlling plant-pathogenic harmful fungi is demonstrated by way of example below:

Example 1

*Phytophthora* Test (Tomato)/Protective

To produce a suitable active ingredient preparation, formulations are suspended with water and diluted to the desired concentration. In the present case, both the known amorphous modification of the substance 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form A), as well as the inventive crystalline form of the substance 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form B) are used as 50 g a.i./liter of SC formulation.

To test for protective effectiveness, young plants are sprayed with the active ingredient preparation at the stated application rate. After initial drying of the spray coating, the plants are inoculated with an aqueous spore suspension of *Phytophthora infestans*. The plants are then placed in an incubation cabin at approx. 20° C. and 100% relative atmospheric humidity.

The evaluation is carried out 3 days after the inoculation. 0% here means an efficacy which corresponds to that of the control, whereas an efficacy of 100% means that no infection is observed.

TABLE A

*Phytophthora* test (tomato)/protective

| Substance | Application rate of active ingredient in ppm | Efficacy in % |
|---|---|---|
| (Form A) SC formulation with amorphous modification of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate | 0.2<br>0.1<br>0.05 | 40<br>15<br>0 |
| (Form B) SC formulation with crystalline modification of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate | 0.2<br>0.1<br>0.05 | 76<br>60<br>40 |

Example 2

*Plasmopara* Test (Vine)/Protective

To produce a suitable active ingredient preparation, formulations are suspended with water and diluted to the desired concentration. In the present case, both the known amorphous modification of the substance 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form A), as well as the inventive crystalline form of the substance 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate (form B) are used as 50 g a.i./liter of SC formulation.

To test for protective effectiveness, young plants are sprayed with the active ingredient preparation at at the stated application rate. After initial drying of the spray coating, the plants are inoculated with an aqueous spore suspension of *Plasmopara viticola* and then remain in an incubation cabin for 1 day at approx. 20° C. and 100% relative atmospheric humidity. The plants are then placed in a greenhouse at approx. 21° C. and approx. 90% atmospheric humidity for 4 days. The plants are then moistened and placed in an incubation cabin for 1 day.

Evaluation is carried out 6 days after the inoculation. 0% here means an efficacy which corresponds to that of the control, whereas an efficacy of 100% means that no infection is observed.

TABLE B

*Plasmopara* test (vine)/protective

| Substance | Application rate of active ingredient in ppm | Efficacy in % |
|---|---|---|
| (Form A) SC formulation with amorphous modification of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate | 0.2<br>0.1<br>0.05 | 35<br>6<br>0 |
| (Form B) SC formulation with crystalline modification of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate | 0.2<br>0.1<br>0.05 | 75<br>35<br>0 |

The invention claimed is:

1. Crystalline form of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethansulphonate, wherein an X-ray powder diffractogram thereof at 25° C. has at least 3 of the following 2Θ (2 theta) values:
$2\Theta = 7.75° \pm 0.2$
$2\Theta = 8.89 \pm 0.2$
$2\Theta = 10.91 \pm 0.2$
$2\Theta = 11.45 \pm 0.2$
$2\Theta = 12.72 \pm 0.2$
$2\Theta = 13.46 \pm 0.2$
$2\Theta = 14.54 \pm 0.2$
$2\Theta = 14.75 \pm 0.2$
$2\Theta = 15.53 \pm 0.2$
$2\Theta = 15.90 \pm 0.2$
$2\Theta = 16.33 \pm 0.2$
$2\Theta = 16.65 \pm 0.2$
$2\Theta = 17.49 \pm 0.2$
$2\Theta = 17.71 \pm 0.2$
$2\Theta = 17.89 \pm 0.2$
$2\Theta = 18.27 \pm 0.2$
$2\Theta = 18.47 \pm 0.2$
$2\Theta = 18.86 \pm 0.2$
$2\Theta = 18.99 \pm 0.2$
$2\Theta = 19.18 \pm 0.2$
$2\Theta = 19.63 \pm 0.2$
$2\Theta = 20.03 \pm 0.2$
$2\Theta = 20.22 \pm 0.2$
$2\Theta = 20.53 \pm 0.2$
$2\Theta = 21.11 \pm 0.2$
$2\Theta = 21.32 \pm 0.2$
$2\Theta = 21.50 \pm 0.2$
$2\Theta = 21.84 \pm 0.2$
$2\Theta = 22.01 \pm 0.2$
$2\Theta = 22.28 \pm 0.2$
$2\Theta = 22.61 \pm 0.2$
$2\Theta = 23.05 \pm 0.2$
$2\Theta = 23.39 \pm 0.2$
$2\Theta = 24.02 \pm 0.2$
$2\Theta = 24.22 \pm 0.2$
$2\Theta = 24.62 \pm 0.2$
$2\Theta = 24.97 \pm 0.2$
$2\Theta = 25.59 \pm 0.2$
$2\Theta = 25.99 \pm 0.2$
$2\Theta = 26.31 \pm 0.2$
$2\Theta = 26.67 \pm 0.2$
$2\Theta = 26.85 \pm 0.2$
$2\Theta = 27.07 \pm 0.2$
$2\Theta = 27.43 \pm 0.2$
$2\Theta = 28.21 \pm 0.2$
$2\Theta = 28.34 \pm 0.2$
$2\Theta = 28.78 \pm 0.2$
$2\Theta = 29.59 \pm 0.2$
$2\Theta = 30.19 \pm 0.2$
$2\Theta = 30.37 \pm 0.2$
$2\Theta = 30.96 \pm 0.2$
$2\Theta = 31.29 \pm 0.2$
$2\Theta = 31.70 \pm 0.2$
$2\Theta = 31.81 \pm 0.2$
$2\Theta = 32.16 \pm 0.2$
$2\Theta = 33.02 \pm 0.2$
$2\Theta = 33.39 \pm 0.2$
$2\Theta = 33.64 \pm 0.2$
$2\Theta = 33.79 \pm 0.2$
$2\Theta = 33.80 \pm 0.2$
$2\Theta = 34.20 \pm 0.2$
$2\Theta = 34.77 \pm 0.2$
$2\Theta = 34.89 \pm 0.2$
$2\Theta = 35.66 \pm 0.2$
$2\Theta = 35.95 \pm 0.2$
$2\Theta = 36.67 \pm 0.2$
$2\Theta = 37.03 \pm 0.2$
$2\Theta = 37.38 \pm 0.2$
$2\Theta = 37.51 \pm 0.2$
$2\Theta = 37.87 \pm 0.2$.

2. Crystalline form according to claim 1, wherein said X-ray powder diffractogram at 25° C. has at least 4 of said 2Θ values.

3. Composition, comprising the novel solid form according to claim 1 and one or more suitable auxiliaries.

4. A crystalline form according to claim 1 capable of being used for preparing a composition for controlling plant-pathogenic harmful fungi in and/or on a plant and/or in and/or on seed of plants.

5. A crystalline form according to claim 1 capable of being used for treating seed.

6. Method for controlling plant-pathogenic harmful fungi in and/or on plants or in and/or on seed of plants, comprising applying the crystalline form according to claim 1 to the plant-pathogenic harmful fungi and/or a habitat thereof and/or to seed.

7. Process for preparing the compound as defined in claim 1 comprising:
   (a) suspending amorphous 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate in a solvent or solvent mixture at temperature of at least 50° C. and
   (b) slowly cooling the suspension.

8. Process according to claim 7, in which the slow cooling is undertaken stepwise.

9. Process according to claim 7, in which the solvent or solvent mixture used is selected from the group consisting of isopropanol, toluene, methyl-THF, diethyl carbonate, chlorobenzene, n-butyl acetate and isobutyl acetate, n-butanol, ethanol, ethyl malonate, methyl t-butyl ether, and also mixtures of toluene and butanol, toluene and n-butyl acetate, ethyl malonate and methyl t-butyl ether, and butyl acetate and methyl t-butyl ether.

10. Process according to claim 8, in which the solvent used is isopropanol.

* * * * *